US005773096A

United States Patent [19]

Hettiarachchi et al.

[11] Patent Number: 5,773,096
[45] Date of Patent: *Jun. 30, 1998

[54] METHOD OF CATALYST PREPARATION BY HIGH-TEMPERATURE HYDROTHERMAL INCORPORATION OF NOBLE METALS ONTO SURFACES AND MATRICES

[75] Inventors: Samson Hettiarachchi, Menlo Park; Thomas Pompilio Diaz, San Martin; John Ewing Weber, Fremont, all of Calif.

[73] Assignee: General Electric Company, Schenectady, N.Y.

[*] Notice: The term of this patent shall not extend beyond the expiration date of Pat. No. 5,600,691.

[21] Appl. No.: 482,224

[22] Filed: Jun. 7, 1995

Related U.S. Application Data

[63] Continuation-in-part of Ser. No. 209,572, Mar. 10, 1994, abandoned, which is a continuation-in-part of Ser. No. 143,513, Oct. 29, 1993, abandoned, and Ser. No. 143,514, Oct. 29, 1993, Pat. No. 5,448,605.

[51] Int. Cl.[6] .................................. B05D 1/18; G21C 9/00
[52] U.S. Cl. ....................... 427/436; 376/301; 376/305; 376/306; 422/11; 422/14; 422/19
[58] Field of Search ........................... 427/436; 376/301, 376/305, 306, 356, 357; 422/11, 14, 19

[56] References Cited

U.S. PATENT DOCUMENTS

| 3,023,085 | 2/1962 | McBride ................................. 23/204 |
| 3,235,392 | 2/1966 | Miles ........................................ 106/1 |
| 3,880,585 | 4/1975 | Hess et al. ............................ 21/2.7 R |
| 4,093,559 | 6/1978 | Fernholz et al. ....................... 252/443 |
| 4,171,393 | 10/1979 | Donley et al. .......................... 427/354 |
| 5,021,269 | 6/1991 | Kono et al. ............................ 427/436 |
| 5,035,875 | 7/1991 | Daish ...................................... 423/580 |
| 5,130,080 | 7/1992 | Niedrach ................................ 376/305 |
| 5,130,081 | 7/1992 | Niedrach ................................ 376/305 |
| 5,135,709 | 8/1992 | Andresen et al. ...................... 376/305 |
| 5,164,152 | 11/1992 | Kim et al. ............................... 376/305 |
| 5,600,691 | 2/1997 | Hettiarachchi et al. ................ 376/305 |
| 5,600,692 | 2/1997 | Hettiarachchi ......................... 376/305 |

FOREIGN PATENT DOCUMENTS

| 0265723 | 5/1988 | European Pat. Off. . |
| 0526160 | 2/1993 | European Pat. Off. . |
| 9218665 | 10/1992 | WIPO . |

OTHER PUBLICATIONS

Derwent Publications Ltd., London, GB; AN 84–059353 & JP–A–59 016 983 (Katayama Kagaku Kogyo Kenkyush), Abstract.

Fontana, Mars G., *Corrosion Engineering*, third edition, 1986, pp. 228–229.

Primary Examiner—Kathryn L. Gorgos
Assistant Examiner—Chrisman D. Carroll
Attorney, Agent, or Firm—Nixon & Vanderhye

[57] ABSTRACT

A method of depositing noble metals on surfaces or matrices to manufacture industrial catalysts that can be used in a variety of applications. Such deposition of noble metals can be achieved by treating the surfaces in high-temperature (150° C. or higher) water containing dissolved noble metal ions or its colloidal suspensions. The method consists of the steps of placing the surface of a metal substrate in contact with a volume filled with high-temperature water; injecting a solution of a noble metal compound into the volume for a predetermined duration; and removing the surface of the metal substrate from contact with the high-temperature water after expiration of said predetermined duration. The noble metal compound has the property that it releases species of the noble metal in high-temperature water. These noble metal species deposit on or incorporate in the oxide film on the surface of the metal substrate.

6 Claims, 5 Drawing Sheets

METHOD OF CATALYST PREPARATION BY HIGH-TEMPERATURE HYDROTHERMAL INCORPORATION OF NOBLE METALS ONTO SURFACES AND MATRICES

RELATED PATENT APPLICATIONS

This application is a continuation-in-part application of U.S. patent application Ser. No. 08/209,572 filed on Mar. 10, 1994, now abandoned which in turn is a continuation-in-part application of U.S. patent application Ser. No. 08/143,513, now abandoned, and Ser. No. 08/143,514, now U.S. Pat. No. 5,448,605, both filed on Oct. 29, 1993.

FIELD OF THE INVENTION

This invention relates to the manufacture of industrial catalysts. In particular, this invention relates to devices having catalytic substrates which catalyze the reaction of two or more molecular species having dilute concentrations in fluids, the breakdown of organic molecules or the conversion of chemicals.

BACKGROUND OF THE INVENTION

Currently, the most commonly used method of industrial catalyst manufacture involves soaking the sub-strate matrix (metal, ceramic or other nonmetallic matrix) in a solution of a noble metal compound, removing the substrate from the solution followed by high-temperature drying in an inert gas, followed by reducing the compound to noble metal. The two processes are alternately repeated in order to increase the catalyst loading on the substrate surface. Such catalysts have been widely used in a variety of industrial applications including the petroleum and nuclear industries. In the petroleum industry, catalysts are used in the cracking of crude oil, whereas in the nuclear industry, catalysts are used in the off gas system as a catalyst for the recombination of $H_2$ and $O_2$ to form water.

A significant problem associated with these catalysts is the catalyst removal from the matrix with time, particularly under fluid-flooded conditions, causing a degradation in the catalytic activity. The reason for this catalyst removal is the poor bonding characteristics between the matrix and the noble metal. Thus, there is a need for a method of manufacturing catalysts whereby the catalytic activity of treated surfaces remains durable over a long period of time even under high-temperature high-velocity flow conditions.

SUMMARY OF THE INVENTION

The present invention is a method of depositing noble metals on surfaces or matrices to manufacture industrial catalysts that can be used in a variety of applications. Such deposition of noble metals can be achieved by treating the surfaces in high-temperature water containing dissolved noble metal atoms or ions or its colloidal suspensions. As used herein, the term "noble metal" means metals from the group consisting of platinum, palladium, osmium, ruthenium, iridium, rhodium, and mixtures thereof; and the term "high-temperature water" means water having a temperature of 150° C. or greater.

Previous studies have shown that the incorporation of noble metals on surfaces or in matrices can be accomplished by this relatively simple hydrothermal treatment. The resulting coated or doped material behaves catalytically in that the treated surfaces have low electrochemical corrosion potentials and very low crack growth rates in high-temperature water containing a stoichiometric excess of dissolved hydrogen. The presence of noble metal on these noble metal-doped surfaces has been proved by surface analysis using Auger spectroscopy and electron spectroscopy for chemical analysis. The amount of noble metal present on these surfaces after doping varies in the range of 2 to 5 atomic % of the noble metal. The noble metal is present to a depth of 200 to 600 angstroms from the top of the surface.

It has also been shown that the noble metal is strongly bonded to the surface by performing ECP measurements of these surfaces after their extensive exposure to high-temperature water under high-flow conditions. The noble metal-doped surfaces remained catalytically active for an extended duration under these conditions.

The method described herein deviates significantly from the conventional methods for imparting catalytic properties onto metal surfaces, such as electroplating and electroless plating. Electroplating requires the use of an externally applied voltage, whereas electroless plating requires the use of strong chemical reducing agents to deposit noble metals on surfaces.

DETAILED DESCRIPTION OF THE PREFERRED EMBODIMENTS

Figure 1:
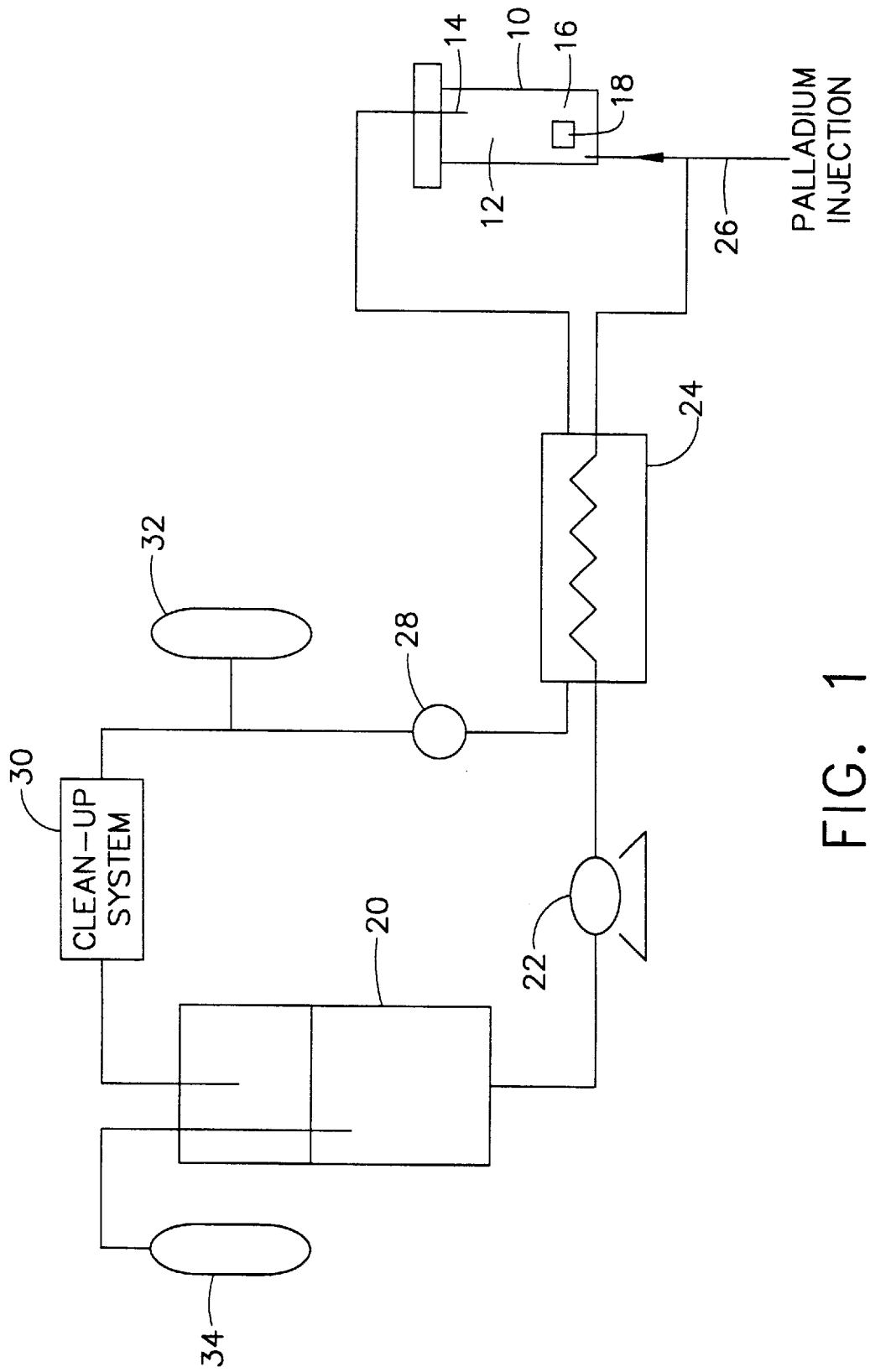
FIG. 1 is a block diagram showing a system for coating or doping a surface or matrix with catalytic material by high-temperature hydrothermal incorporation in accordance with the present invention.

The present invention is directed to a method for coating or doping a metal structure with catalytic material, e.g., platinum, palladium and other noble metals. Referring to FIG. 1, the system for applying the catalyst in accordance with a preferred embodiment is a recirculating flow loop comprising a heated high pressure vessel 10, e.g., an autoclave. The vessel has an inlet 12 and an outlet 14 which are in flow communication with a chamber 16 inside vessel 10. The matrix 18 to be coated or doped with noble metal is placed inside the vessel. The vessel inlet 12 is connected to an outlet at the bottom of a water tank 20 via a recirculation pump 22 and a heat exchanger 24. The vessel 10 has a heater capable of heating the water in chamber 16 to a temperature sufficient to cause thermal decomposition of a noble metal compound which is injected at injection point 26 located downstream of heat exchanger 24 directly into the heated high-pressure vessel 10. The heated water inside chamber 16 is returned to the water tank 20 via heat exchanger 24, a backpressure regulator 28 and a water cleanup system 30.

The heat exchanger transfers heat from the hot water exiting vessel 10 to the cold water entering vessel 10, whereby the incoming water is pre-heated. A chemical analysis system 32 may be used to sample the water exiting the vessel 10 and determine the noble metal content by a conventional chemical analysis technique.

In accordance with the method of the present invention, the matrix 18 to be treated has oxidized surfaces. Preferably, the water temperature inside the vessel 10 is at least 150° C., preferably 288° C. (the pressure is preferably about 1200 psi). The noble metal compound is injected in the form of a solution or a colloidal suspension. As used herein, the term "solution" means both solutions and colloidal suspensions. The noble metal compound releases species of the noble metal into the high-temperature water. As used herein, the term "species" means atoms, ions and molecules.

The preferred noble metal compound is $Na_2Pt(OH)_6$. Another suitable compound for use in the invention is palladium acetylacetonate ($Pd(CH_3COCHCOCH_3)_2$), an organometallic compound, which undergoes thermal decomposition in high-temperature water, thereby releasing palladium atoms which deposit on oxidized surfaces. Alternatively, palladium nitrate, which releases palladium ions upon ionization in high-temperature water, can be used. Other suitable noble metal compounds are $K_3Rh(NO_2)_6$, $Pt(NH_3)_4(NO_2)_3$ and mixtures of $Na_2Pt(OH)_6$ and $K_3Rh(NO_2)_6$. As used herein, the term "release" also includes the colloidal formation of noble metal molecules. The concentration of palladium in the reactor water is preferably in the range of 5 to 100 ppb. Doping occurs when palladium atoms, ions or molecules (i.e., species) released into the high-temperature water deposit on the oxidized surfaces of the flooded reactor components.

To demonstrate the viability of the method for preparing catalysts in accordance with the present invention, experiments were conducted in which an auto-clave made of oxidized Type 304 stainless steel was doped with palladium by high-temperature hydrothermal incorporation. Type 304 stainless steel is typically 18–20% Cr, 8–12% Ni, 1% Si max., 0.08% C max., and balance Fe. The noble metal doping was performed by injecting a palladium nitrate hydrate solution into the autoclave containing high-temperature water at 288° C. The palladium injection was performed over a period of 48 hr. After injecting the palladium solution over this period of time, the water flow through the autoclave was continued until the system was cleaned up of the added noble metal compound.

Subsequently, an oxygen/hydrogen recombination test was performed to determine the recombination efficiency of the catalytic autoclave surface. The autoclave flow during the test was approximately 2.3 to 3.4 gpm. Hydrogen and oxygen were injected into the water flowing through the autoclave and the exiting dissolved gas content was analyzed to determine the effectiveness of the recombination process. Oxygen and hydrogen are expected to recombine on a catalyst surface to form water according to their molar ratio of 1 to 2 (or a mass ratio of O:H of 8:1) respectively. If the catalyst is 100% effective, recombination should occur according to this ratio at 100% efficiency. Thus, the recombination efficiency is an indication of the catalytic activity of the surface.

Figure 2:
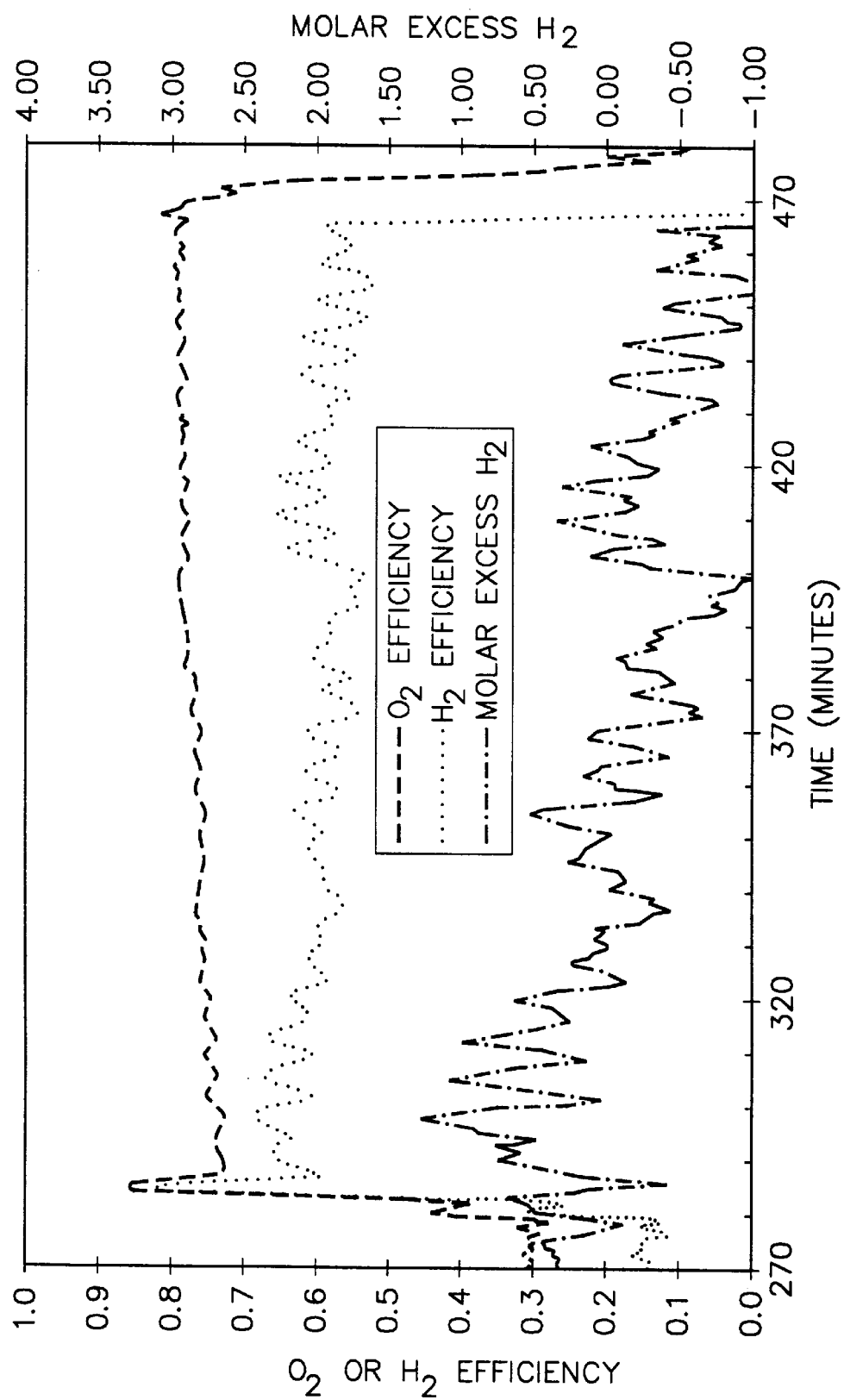
FIG. 2 is a graph of hydrogen/oxygen recombination efficiency and molar excess hydrogen on a surface which has been doped with noble metal in accordance with the present invention.

FIG. 2 shows the efficiency with which the noble metal-doped autoclave surface recombines oxygen with hydrogen. From FIG. 2, it is clear that the efficiency of oxygen recombination is around 73 to 80%, whereas the efficiency of hydrogen recombination is 55 to 66%. The lower end of the recombination efficiency is due to the sub-stoichiometric conditions of $H_2$ to $O_2$, whereas the higher end of the efficiency corresponds to the stoichiometric or super-stoichiometric conditions. The deviation from 100% efficiency is attributed to the poor surface area-to-volume ratio existing inside the auto-clave.

Figure 3:
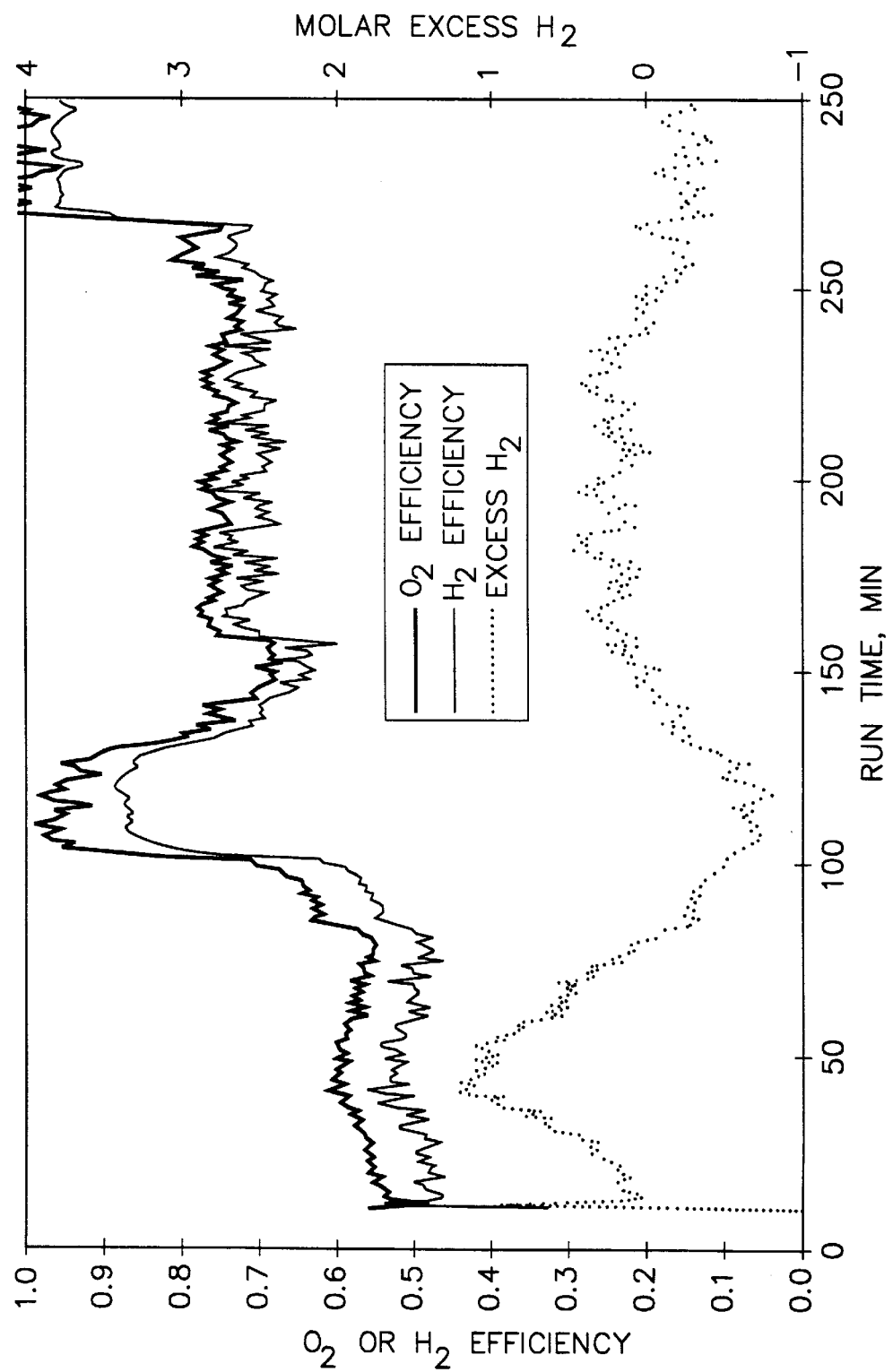
FIG. 3 is a graph of hydrogen/oxygen recombination efficiency and molar excess hydrogen on a pure palladium surface crimped to have a high surface area.

FIG. 3 shows the $H_2$ to $O_2$ recombination efficiency for a 100% palladium crimped ribbon configuration. Because of the crimping and the presence of 100% noble metal, the recombination efficiency, in this case, is expected to be higher. The average oxygen recombination efficiency with this material is 55 to 75%, whereas that for hydrogen recombination is around 50 to 80%, except for very short periods when the efficiencies were in the 90 to 100% range. Thus, it is clear from this result that despite using pure palladium ribbon with a higher surface area to volume ratio, the recombination efficiencies for both oxygen and hydrogen are similar to that obtained with the palladium-doped autoclave which had a much lower surface area to volume ratio, confirming the viability of using the noble metal chemical addition technology of the present invention for catalyst manufacture. It is believed that with a properly optimized surface (i.e. high surface area to volume ratio), noble metal chemical addition technology has a great potential of providing almost theoretical efficiencies for recombination of hydrogen and oxygen using very small amounts of the noble metal (e.g., 2 to 3 atomic % of the noble metal to a depth of 200 to 600 angstroms). This fact can be used for fabricating recombination catalysts for the off-gas system and for internal catalytic recombiners of boiling water nuclear reactors. In addition, this method of fabrication should yield effective catalysts that can be used for even non-nuclear applications such as in petroleum cracking and other chemical technologies.

Figures 4A, 4B:
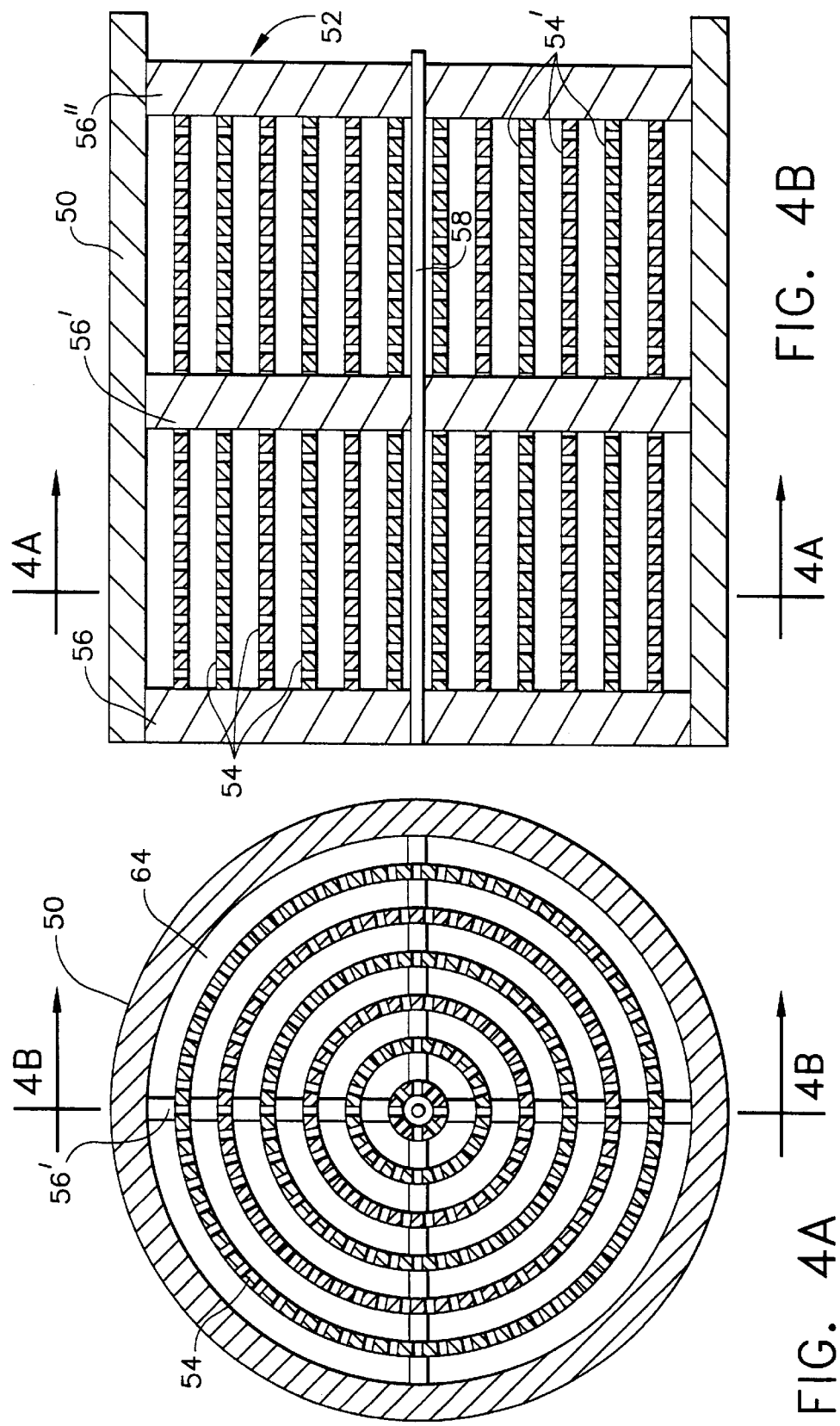
FIGS. 4A and 4B are transverse and longitudinal sectional views respectively of an exemplary catalytic recombiner cartridge installed in a pipe, the cartridge incorporating a metal structure having a surface area coated or doped with noble metal in accordance with the present invention.

A typical catalytic recombiner structure, having surfaces which can be doped with noble metal using the present invention, is depicted in FIGS. 4A and 4B. The apparatus is a catalytic recombiner installed upstream of the piping or other system requiring SCC protection. The recombiner will facilitate the reaction of a small (stoichiometric) hydrogen addition with the dissolved oxygen and hydrogen peroxide present in the water entering the selected system. Thus, the ECP of the water exiting the recombiner will be reduced below the SCC threshold value and SCC will be prevented downstream of the recombiner at all system locations up to the point where the water either mixes with coolant containing higher concentrations of oxygen and/or hydrogen peroxide, or again passes through the reactor core, where radiolysis reoccurs.

The catalytic recombiner shown in FIGS. 4A and 4B is generally constructed from a material with a catalytically active surface that facilitates the recombination of dissolved oxygen and hydrogen peroxide with hydrogen, which is added as a gas to the water upstream of the recombiner. To increase the catalytic recombiner efficiency, the active surface area must be maximized per unit flow volume, consistent with the allowed system pressure drop. For any given system being protected, the allowable pressure drop increase due to the presence of the recombiner is set by the system design.

To accomplish this chemical reaction process, the recombiner has a high surface-to-volume ratio and is constructed from a non-noble metal alloy coated or doped with noble metal, which is known to be an efficient water recombination catalyst in high-temperature water. In particular, the recombiner may be constructed of relatively thin metal sheets of inexpensive oxidized stainless steel coated or doped with noble metal in accordance with the technique of the present invention. These noble metal-doped sheets may be fabricated into shells, plates, Swiss roll configurations (including metal meshes) or continuous strips and configured to allow insertion into the upstream portion of the system to be protected. The recombiner may take the form of a cartridge of compact, rugged, modular design that can be designed for a wide range of pipe sizes and flow velocities. The recombiner structure includes means for mixing reactants between channels of the mass exchanger, thereby minimizing segregation and enhancing overall efficiency.

The catalytic recombiner is arranged and situated such that all (except perhaps a small leakage flow) water phase which ultimately flows through the component to be protected will first flow over the surfaces of the catalytic material. The catalytic surfaces react with the water radiolysis products $O_2$ and $H_2O_2$ in the liquid phase to form $H_2O$ in accordance with reactions such as (but not limited to) the following:

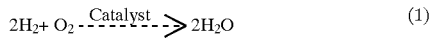   (1)

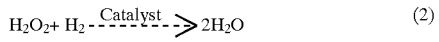   (2)

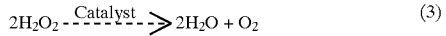   (3)

Reaction (3) is followed by reaction (1) to produce water. Thus, the catalytic recombiner provides a means for substantially reducing oxygen concentration in fluids, thereby lowering the ECP and reducing the like-lihood of SCC in susceptible downstream components.

Although the catalytic recombiner is disclosed in the context of BWRs, it can be used with compressible or incompressible fluids, such as air or water at elevated temperatures, in a variety of technical applications that involve the catalytic reaction of undesirable compounds in solution. For example, the principle of the invention can be applied in systems for converting CO in exhaust systems (such as catalytic converters on automobiles) or systems for converting $CO_2$ into $H_2O$(such as scrubbers in fossil fuel plants).

The catalytic recombiner cartridge 52 depicted in FIGS. 4A and 4B is suitable for installation in a pipe 50 of circular cross section. This exemplary catalytic recombiner cartridge comprises a first plurality of concentric thin cylindrical shells 54 supported between spacers 56 and 56' and a second plurality of concentric thin cylindrical shells 54' supported between spacers 56' and 56", for example, by spot welding or brazing. Each spacer comprises a number (e.g., four) of planar fins, each fin being welded at one end to a central rod 58 positioned along the axis of the concentric shells. Rod 58 resists torquing of the spacers relative to each other.

The surfaces of the catalytic recombiner parts may be treated using noble metal chemical addition technology either before or after assembly. In accordance with a preferred embodiment, the cylindrical shells 54 are formed from thin sheets (e.g., 10–12 mils thick) of stainless steel coated or doped with palladium. Each shell is provided with a multiplicity of means for generating turbulence. The spacers and central rod may also be coated or doped with noble metal before assembly. Then the sheets are rolled into a cylindrical shape and then welded (not shown) along the overlapping edges to form a cylindrical shell. The cylindrical shells are then welded (not shown) to the supporting structure, i.e., spacers 56, 56' and 56" welded to central rod 58, to form a cartridge 52 which is installed inside pipe 50 with the surfaces of shells 54 lying generally parallel to the direction of fluid flow. The spacers function to stiffen the concentric shells against flow-induced vibration and to maintain the shells in concentric relationship with channels 64.

After the catalytic recombiner cartridge has been installed in the reactor piping, $H_2$ gas is injected into the flow at a point immediately upstream of installed cartridge 52. The fluid flowing through pipe 50 should be $H_2$-enriched to provide an adequate supply of $H_2$ for the catalytic recombination of dissolved $H_2$ and $O_2$ to form water at the surfaces of shells 54. As a result of this catalytic recombination, the concentrations of $O_2$ and $H_2O_2$ in the fluid exiting cartridge 52 will be reduced to a level where the ECP is below the SCC threshold value, thereby reducing the susceptibility to SCC of components immediately downstream of the cartridge.

Figure 5:
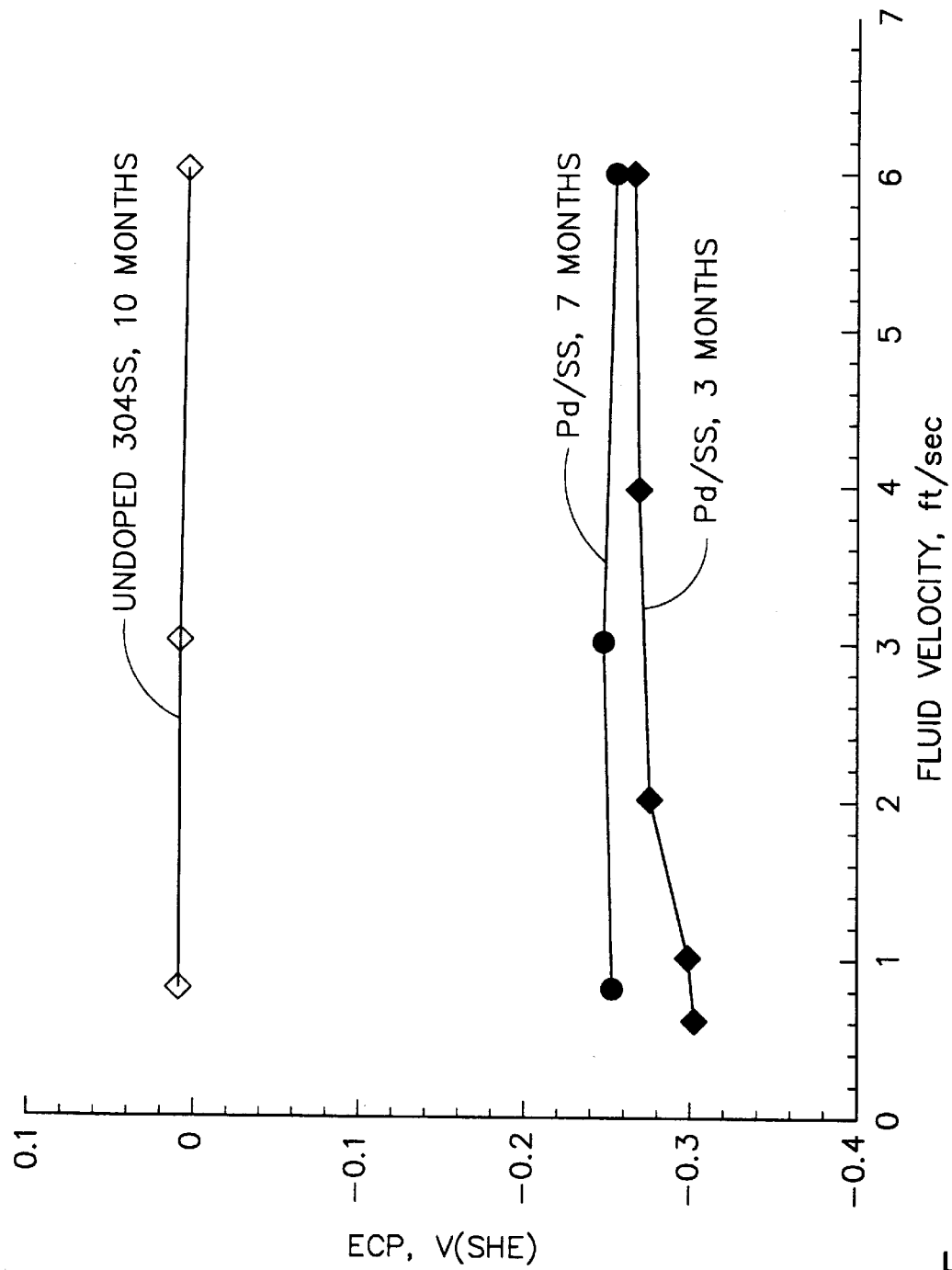
FIG. 5 is a graph of electrochemical potential as a function of fluid velocity for palladium-doped stainless steel after 3 (♦) and 6 (●) months and undoped stainless steel after 10 months (◊) in high-temperature (540° F.), high-velocity (6ft/sec) flow with an average $H_2/O_2$ ratio of 14.

The method of the present invention can be used to provide stable and durable catalytic surfaces on the internal surfaces of a catalytic recombiner cartridge or any other catalytic reactor. The catalytic material deposited by high-temperature hydrothermal incorporation forms a strong bond with the oxide film on the substrate that resists catalyst removal from the substrate over time, particularly when exposed to high-velocity fluid flow inside the piping of a nuclear reactor power plant, as shown by the experimental data in FIG. 5. The data for palladium-doped stainless after 3 and 7 months in high-temperature, high velocity flow shows a very small difference in ECP response. This indicates the presence of noble metal even after 7 months of exposure at 540° F. at 6 ft/sec fluid velocity. If noble metal had been removed by the high-velocity flow, then the response should be similar to the data shown for undoped stainless steel. Thus, the invention enables the manufacture of stable catalysts which will not experience a degradation in catalytic activity over time.

The foregoing method of preparing catalytic structures has been disclosed for the purpose of illustration. Variations on and modifications to the disclosed method will be readily apparent to practitioners skilled in the design of catalytic reactors. All such variations and modifications are intended to be encompassed by the claims set forth hereinafter.

We claim:

1. A method for applying a noble metal on an oxided surface of a metal substrate, comprising the steps of:

placing the surface of the metal substrate in contact with a volume filled with high-temperature water;

injecting a solution of a noble metal compound into said volume for a preset duration;

causing said noble metal compound to decompose in said high-temperature water to release species of said noble metal which incorporate in said oxided surface of said metal substrate; and removing the surface of the metal substrate from contact with the high-temperature water after expiration of said preset duration.

2. The method as defined in claim 1, wherein said noble metal is palladium.

3. The method as defined in claim 1, wherein said noble metal is platinum.

4. The method as defined in claim 1, wherein said noble metal compound is injected into said high-temperature water in an amount sufficient to produce a noble metal concentration of 5 to 100 ppb.

5. The method as defined in claim 1, wherein said high-temperature water has a pressure greater than 1 atm and a temperature equal to at least about 150° C.

6. The method as defined in claim 5, wherein said high-temperature water has a pressure of about 1200 psi and a temperature of about 288° C.

* * * * *